United States Patent [19]

Nicholas et al.

[11] Patent Number: 5,588,962
[45] Date of Patent: Dec. 31, 1996

[54] DRUG TREATMENT OF DISEASED SITES DEEP WITHIN THE BODY

[75] Inventors: Peter M. Nicholas, South Dartmouth; Ronald A. Sahatjian, Lexington; James J. Barry, Marlborough, all of Mass.

[73] Assignee: Boston Scientific Corporation, Natick, Mass.

[21] Appl. No.: 219,108

[22] Filed: Mar. 29, 1994

[51] Int. Cl.$^6$ ..................................................... A61N 1/30
[52] U.S. Cl. .......................... 604/52; 604/19; 604/53; 128/898
[58] Field of Search ................................ 604/20, 53, 96, 604/99, 265–266, 890.1, 892.1, 52, 21, 22; 606/192, 194; 128/898; 424/443, 445, 423–426

[56] References Cited

U.S. PATENT DOCUMENTS

| | | |
|---|---|---|
| 3,699,956 | 10/1972 | Kitrilakis et al. . |
| 4,026,296 | 5/1977 | Stoy et al. . |
| 4,299,226 | 11/1981 | Banka . |
| 4,330,497 | 5/1982 | Agdanowksi . |
| 4,364,392 | 12/1982 | Strother et al. . |
| 4,417,576 | 11/1983 | Baran . |
| 4,423,725 | 1/1984 | Baran et al. . |
| 4,448,195 | 5/1984 | LeVeen et al. . |
| 4,481,323 | 11/1984 | Sterling . |

(List continued on next page.)

FOREIGN PATENT DOCUMENTS

| | | |
|---|---|---|
| 0372088A1 | 6/1990 | European Pat. Off. . |
| 0379156A2 | 7/1990 | European Pat. Off. . |
| 0399712A1 | 11/1990 | European Pat. Off. . |
| 0166998B1 | 5/1991 | European Pat. Off. . |
| 0526102A1 | 2/1993 | European Pat. Off. . |

(List continued on next page.)

OTHER PUBLICATIONS

McMath et al., "Experimental Application of Bioprotective Materials to Injured Arterial Surfaces with Laser Balloon Angioplasty", *Circulation* (Supp. III) 82:0282 (abstract) (Oct. 1990).

Thompson et al., "Heparin and Growth Control of Vascular Cells," *Ann. N.Y. Acad. Sci.* 556:255–267 (1989).

Tidd et al., "Comparison of Hydrophilic Polymer–Coated Latex, uncoated Latex and PVC Indwelling Balloon Catheters in the Prevention of Urinary Infection," *J.Urol.* 48:285–291 (1976).

Waller et al., "Vessel Wall Pathology After Angioplasty," *Cardio.* 57, 60, 69–72, 81 (Aug. 1990).

Waller et al., "Morphologic Observations Late after Coronary Balloon Angioplasty Mechanisms of Acute Injury and Relationship to Restenosis," *Radio.* 174:961–967 (Mar. 1990).

The Andreas Gruentzig Cardiovascular Center News Letter (Spring 1990).

European search report dated Sep. 15, 1993.

Deutsch et al., "Low Stress Angioplasty at 60° C: Attenuated Arterial Barotrauma".

International Search Report for International Application No. PCT/US91/09804.

Wolinsky et al., "Local Introduction of Drugs into the Arterial Wall: A Percutaneous Catheter Technique".

Chapman et al., "A Bioabsorbable Stent: Initial Experimental Results", *Circulation* (Supp III) 82:0283 (abstract) (Oct. 1990).

(List continued on next page.)

*Primary Examiner*—Corrine M. McDermott
*Assistant Examiner*—Chalin Smith
*Attorney, Agent, or Firm*—Fish & Richardson P.C.

[57] ABSTRACT

A diseased site, such as vascular dilatation site, is treated by first locally delivering to the site an agent that is effective to localize a desired drug and then systematically administering the drug.

27 Claims, 4 Drawing Sheets

U.S. PATENT DOCUMENTS

| | | | |
|---|---|---|---|
| 4,515,593 | 5/1985 | Norton . | |
| 4,589,873 | 5/1986 | Schwartz et al. . | |
| 4,592,340 | 6/1986 | Boyles . | |
| 4,603,152 | 7/1986 | Laurin et al. . | |
| 4,693,243 | 9/1987 | Buras . | |
| 4,714,460 | 12/1987 | Calderon . | |
| 4,769,013 | 9/1988 | Lorenz et al. . | |
| 4,784,647 | 11/1988 | Gross . | |
| 4,820,270 | 4/1989 | Hardcastle et al. . | |
| 4,832,688 | 5/1989 | Sagae et al. . | |
| 4,876,126 | 10/1989 | Takemura et al. . | |
| 4,909,258 | 3/1990 | Kuntz et al. . | |
| 4,923,450 | 5/1990 | Maeda et al. . | |
| 4,932,934 | 6/1990 | Dougherty et al. | 604/21 |
| 4,950,256 | 8/1990 | Luther et al. . | |
| 4,955,377 | 9/1990 | Lennox et al. . | |
| 4,983,166 | 1/1991 | Yamawaki . | |
| 4,993,412 | 2/1991 | Murphy-Chuorian . | |
| 4,994,033 | 2/1991 | Shockey et al. . | |
| 5,021,044 | 6/1991 | Sharkawy . | |
| 5,026,607 | 6/1991 | Kiezulas . | |
| 5,041,100 | 8/1991 | Rowland et al. | 604/265 |
| 5,047,045 | 9/1991 | Arney et al. . | |
| 5,049,132 | 9/1991 | Shaffer et al. . | |
| 5,091,205 | 2/1992 | Fan . | |
| 5,102,402 | 4/1992 | Dror et al. . | |
| 5,120,322 | 6/1992 | Davis et al. . | |
| 5,135,516 | 8/1992 | Sahtjian et al. | 604/265 |
| 5,163,906 | 11/1992 | Ahmadi . | |
| 5,167,960 | 12/1992 | Ito et al. | 424/423 |
| 5,171,217 | 12/1992 | March et al. | 604/53 |
| 5,180,366 | 1/1993 | Woods . | |
| 5,199,951 | 4/1993 | Spears | 604/96 |
| 5,209,720 | 5/1993 | Unger | 604/22 |
| 5,213,576 | 5/1993 | Abiuso et al. . | |
| 5,213,580 | 5/1993 | Slepian et al. . | |
| 5,226,430 | 7/1993 | Spears | 128/898 |
| 5,232,444 | 8/1993 | Just et al. . | |
| 5,252,557 | 10/1993 | Kita et al. | 514/8 |
| 5,286,254 | 2/1994 | Shapland et al. | 604/21 |
| 5,295,944 | 3/1994 | Teicher et al. | 600/1 |
| 5,298,018 | 3/1994 | Narciso, Jr. | 604/21 |
| 5,301,688 | 4/1994 | Stephen et al. | 607/99 |
| 5,304,121 | 4/1994 | Sahatjian . | |
| 5,328,471 | 7/1994 | Slepian | 604/101 |
| 5,356,433 | 10/1994 | Rowland et al. | 623/11 |
| 5,376,376 | 12/1994 | Li | 424/443 |
| 5,409,012 | 4/1995 | Sahatjian . | |
| 5,470,307 | 11/1995 | Lindall | 604/20 |

FOREIGN PATENT DOCUMENTS

| | | |
|---|---|---|
| 380205 | 1/1924 | Germany . |
| 1196327 | 7/1965 | Germany . |
| 53006430 | 1/1978 | Japan . |
| 54-35036 | 10/1979 | Japan . |
| 1069826 | 1/1984 | U.S.S.R. . |
| 2112646 | 7/1983 | United Kingdom . |
| 0166998B1 | 1/1986 | WIPO . |
| WO89/12478 | 12/1989 | WIPO . |
| WO91/08790 | 6/1991 | WIPO . |
| WO92/11895 | 7/1992 | WIPO . |
| WO92/11896 | 7/1992 | WIPO . |
| WO93/06792 | 4/1993 | WIPO . |
| WO93/11751 | 6/1993 | WIPO . |

OTHER PUBLICATIONS

Guyton et al., "Inhibition of Rat Arterial Smooth Muscle Cell Proliferation by Heparin: In Vivo Studies with Anticoagulant and Nonanticoagulatn Heparin," *Circ. Res.* 46:625–634 (May 1980).

Guyton et al., "Inhibition of Rat Arterial Smooth Muscle Cell Proliferation by Heparin: In Vivo Studies with Anticoagulant and Nonanticoagulant Heparin," *Circ. Res.* 46:625–634 (May 1980).

Shibasaki et al., "Effects of Cimetidine on Lidocaine Distribution in Rats", 1988, *J. Pharmacobio–Dyn.*, 11(12):785–93.

DRUG TREATMENT OF DISEASED SITES DEEP WITHIN THE BODY

FIELD OF THE INVENTION

This invention relates to treating diseased sites that are deep within the body with drugs.

BACKGROUND OF THE INVENTION

In vascular angioplasty, a balloon catheter is threaded through a vascular lumen to the site of an occlusion. The balloon is inflated at the site to widen the lumen and then deflated and removed from the body. However, in time, the site may restenose. The restenosis may occur because the angioplasty procedure sometimes creates cracks in plaque on the vessel wall which leave jagged surfaces that can induce blood clotting at the site. Another cause of restenosis is the development of intimal proliferation. This condition is characterized by excessive cell growth that is triggered by the trauma of the angioplasty treatment.

Drugs can be administered to treat the restenosed site. One method is to administer the drug systemically, e.g., orally or intravenously. In this case, a relatively large amount of drug must be administered so that, after being diluted during transport through the body, an effective dose reaches the site. Moreover, many parts of the body which are not diseased are still exposed to the drug. Another method for administering the drug is to carry it through the body on a medical device and then release it locally at the site. In this case, the patient must suffer the discomfort and risk of a medical procedure. Moreover, the medical device must be placed in the body each time the drug is administered.

SUMMARY OF THE INVENTION

In this invention, the diseased site, typically an angioplasty site, is treated by first locally delivering to the site an agent that is effective to localize a desired drug and then systematically administering the drug.

In a first aspect, the invention features treating a diseased site deep within the body by locally delivering to the diseased site a drug-localizing agent using a medical device capable of carrying the agent to and releasing the agent at the site in a manner that the agent is retained at the site, removing the medical device from the body, and systemically delivering drug which is localized at the site by the presence of the localizing agent.

In another aspect, the invention features a method for treating a diseased site in a vascular lumen deep within the body of a patient by providing a drug-localizing agent for a drug that is effective to treat the diseased site, providing a medical device capable of being placed into the vascular lumen at the diseased site and capable of delivering the localizing agent locally at the site, preparing the medical device for delivering the agent at the site, placing the medical device at the site, locally delivering the agent to the site in a manner that the agent is retained at the site, removing the medical device from the vascular lumen, and monitoring the patient for symptoms of restenosis after removing the medical device from the vascular lumen.

In another aspect, the invention features treating a diseased site in a vascular lumen deep within the body of a patient by providing a drug-localizing agent for a drug that is effective to treat the diseased site, providing a medical device capable of being placed into the vascular lumen at the diseased site and capable of delivering the localizing agent locally at the site, preparing the medical device for delivering the agent at the site, placing the medical device at the site, locally delivering the agent to the site in a manner that the agent is retained at the site, removing the medical device from the vascular lumen, providing the drug effective to treat the diseased site in a form suitable for systemic administration, systematically administering the drug so the the drug is transported through the body of the patient and concentrated at the diseased site by the presence of the drug-localizing agent retained at the site.

In another aspect, the invention features a kit for treating a diseased site in a vascular lumen deep within the body of a patient. The kit has a drug-localizing agent for a drug that is effective to treat the diseased site, a medical device capable of being placed into the vascular lumen at the diseased site and capable of delivering the localizing agent locally at the site in a manner that the agent is retained at the site. In embodiments, the kit may also include a drug effective to treat the diseased site in a form suitable for systemic administration so the the drug is transported through the body of the patient and localized at the diseased site by the presence of the drug-localizing agent retained at the site.

Embodiments may include one or more of the following features. The drug forms a chemical complex with the drug-localizing agent. The drug is an anionic species and the agent is a cationic species in the body lumen environment of the site. The drug is heparin. The agent is an ammonium cation. The agent is benzalkonium cation. The localizing agent is cimetidine and the drug is lidocaine. The agent is an adhesive polymer that adheres to the site and incorporates a specie that forms a complex with the drug. The treatment includes delivering the agent to the site under pressure. The treatment includes delivering the agent to the site with the aid of heat. The treatment includes monitoring the patient for symptoms of restenosis after removing the medical device from the vascular lumen and providing and administering the drug after observation of the symptoms. The treatment includes delivering the agent simultaneously with the dilatation of the diseased site. The treatment includes delivering the agent simultaneously with locally administering a drug for initially treating the site. The treatment includes locally administering the same drug that is to be administered systemically. The treatment includes locally delivering a sufficient amount of the agent to localize an effective amount of the drug from multiple sequential systemic administrations, and systematically administering a sufficient quantity of the drug in a sequential fashion as needed to effectively treat the site. The treatment includes after systemically delivering a desired drug, delivering additional drug-localizing agent locally to the diseased site and, thereafter, systemically delivering additional desired drug. The treament includes delivering a mixture of drug-localizing agents effective to concentrate different drugs and systemically administering the drugs as desired. The medical device is a dilatation catheter having an expandable portion. The expandable portion includes a compressible polymer capable of releasing the agent when compressed. The polymer is a hydrogel. The expandable portion includes openings, pores or channels through which the agent may pass to deliver the agent to the site.

The inventions have many advantages. For example, in embodiments, the localizing agent can be delivered simultaneously with dilatation of a stenosis using an angioplasty balloon. Afterwards, if the patient does not develop a condition which requires drug treatment, such as restenosis, then the physician can elect to forego delivering any drug and thus avoid needlessly subjecting the patient to a physiologically active substance. The physiologically inocuous localizing agent is eventually metabolized as the patient recovers. If, on the other hand, the patient develops restenosis and a drug treatment becomes desired, the drug can be administered systemically. This avoids subjecting the patient to another body-invasive operation to locally deliver the drug. Moreover, the amount of drug administered may be less than ordinary systemic treatments because the agent concentrates or improves the efficacy of the drug at the site. This can also expand the types of drugs which can be delivered systemically to those that would otherwise require administration at high or even toxic levels to ensure that an effective dose reaches the site. Further, if subsequent additional drug administrations become desirable, they might also be done systematically without delivering additional agent to the site.

Other aspects and advantages follow.

BRIEF DESCRIPTION OF THE DRAWING

We first briefly described the drawings.

FIGS. 1–7a illustrate the structure and a use of an embodiment of the invention.

DESCRIPTION OF THE PREFERRED EMBODIMENTS

Figure 1:
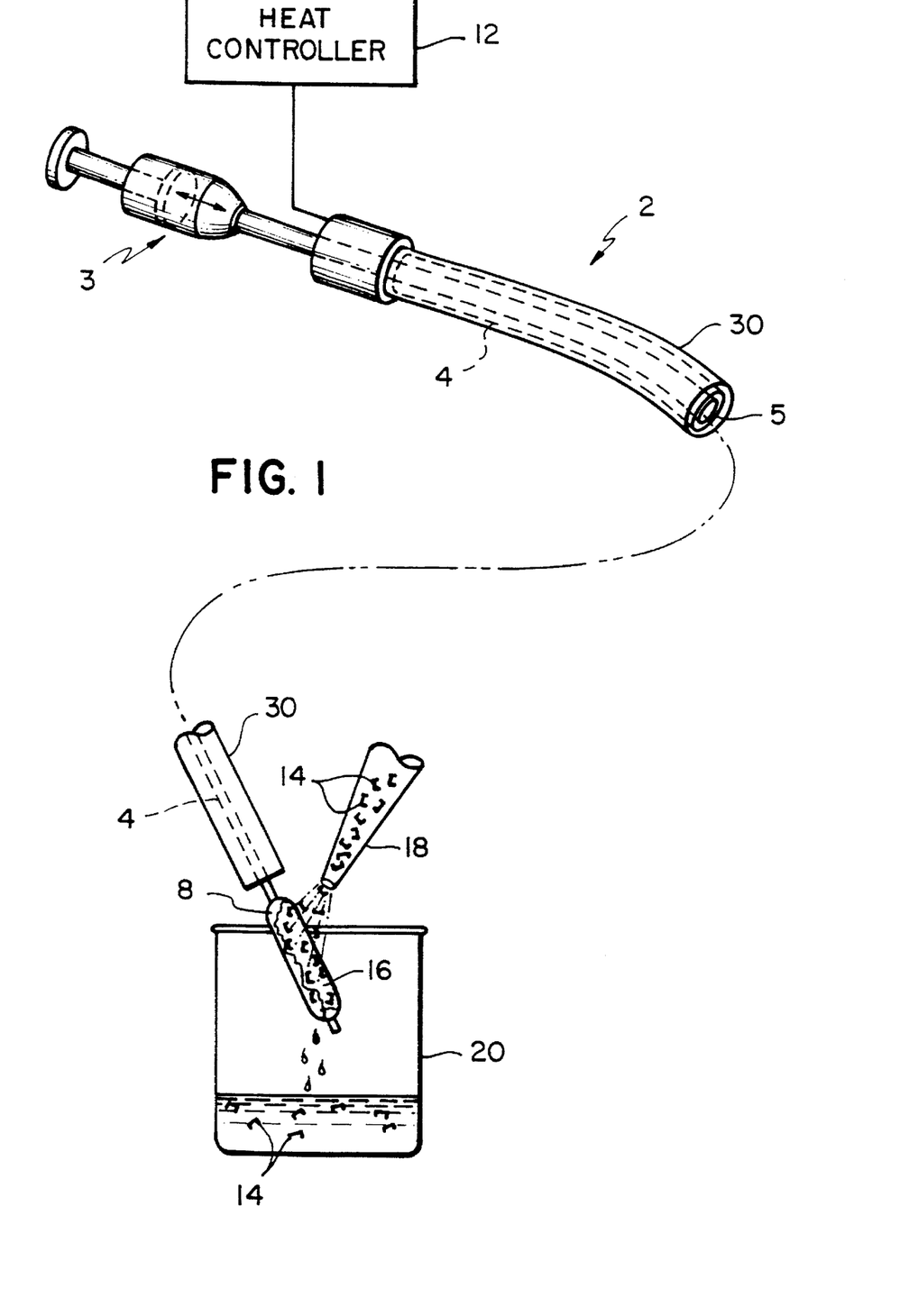

Referring to the figures, particularly to FIG. 1, which is a schematic of a drug-localizing agent delivery apparatus 2 being prepared for use in a vascular lumen, the apparatus 2 includes a catheter 4 that is constructed to be threaded through a blood vessel. The catheter 4 includes nears its distal end an expandable portion, which may be, for example, a balloon 8. The balloon 8 is inflated and deflated by injecting or withdrawing fluid from a source 3 through a lumen 5 in the catheter to a port 10 located within the balloon (see also, e.g., FIG. 2a). The catheter 4 is constructed to apply heat to a diseased site by heating the balloon during inflation. The amount of heat can be controlled from outside the body using a heat controller 12. The apparatus 2 may also include an axially moveable protective sheath 30 that can be extended over the balloon while the apparatus is threaded into and out of the body. (The sheath may also be a separate, axially stationary introducer catheter of the type used to direct angioplasty catheters to the coronary arteries.)

In this embodiment, the balloon 8 includes a coating 16, which is preferably a swellable, compressible hydrogel that can carry the agent to the site and then release it when the hydrogel is compressed against the lumen wall by balloon inflation. The catheter 4 is prepared by flowing a solution that includes the agent 14 (denoted schematically by []) from a spray bottle 18 over the coating 16. Excess solution is collected in a suitable receptacle 20 for later use in other operations. (The balloon with the coating could as well be dipped in the solution.) In this embodiment, the localizing agent is benzalkonium cation which forms a chemical complex with, and hence tends to localize, the drug heparin. The benzalkonium cation is applied as an aqueous solution of benzalkonium chloride which is absorbed by the hydrogel coating.

Figures 2, 2A, 3, 3A:
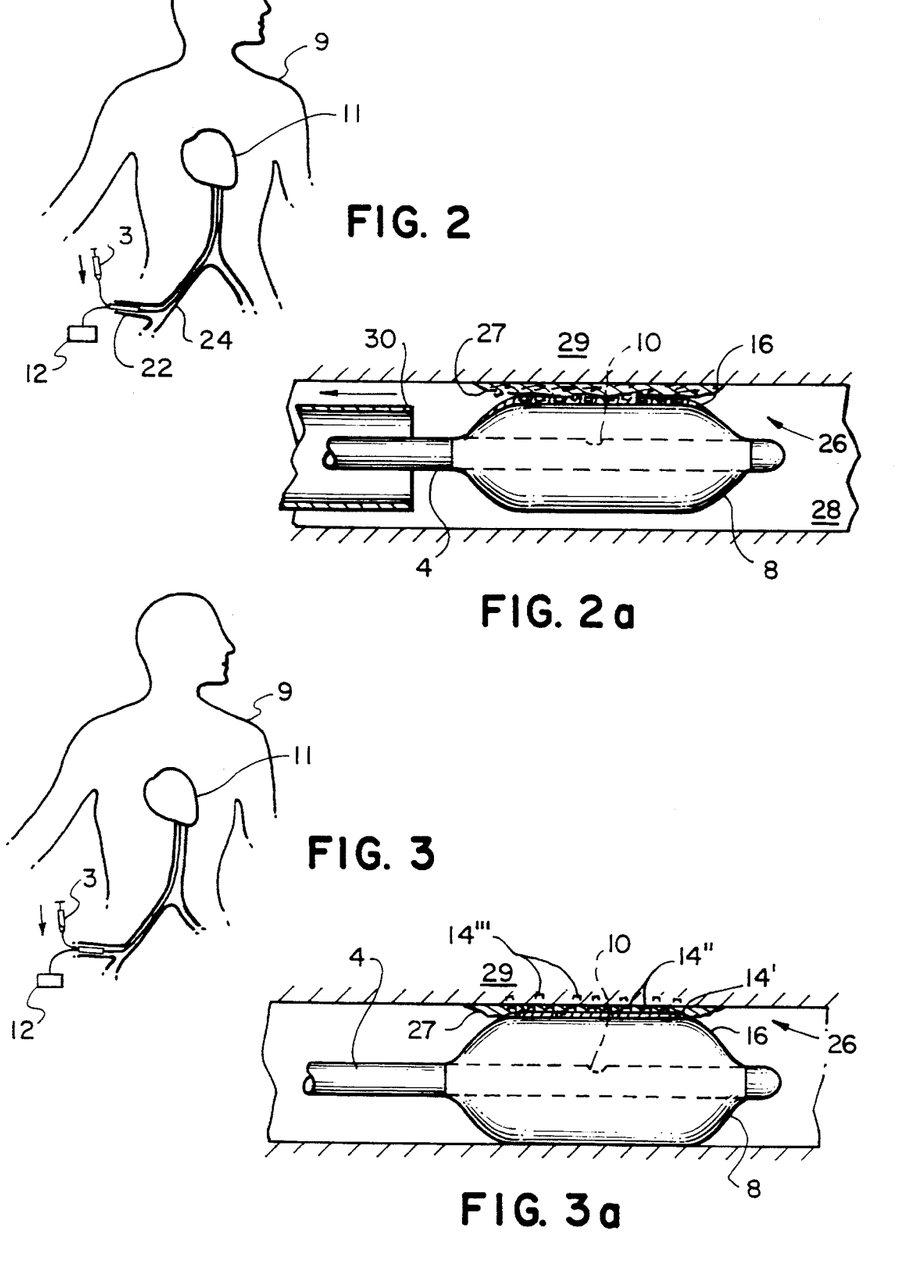

Referring to FIG. 2, a schematic of a patient 9, the apparatus 2 is delivered through an access catheter 22 in the groin to the femoral artery 24, and threaded through the vascular system to, for example, a site of a vascular occlusion in a coronary artery of the heart 11.

Referring as well to FIG. 2a, which is a greatly enlarged view of the distal end of the apparatus inside the body, the site 26 in the coronary artery 28 is occluded by plaque 27 on the wall. To dilate the site and simultaneously deliver the localizing agent, the sheath 30 is withdrawn to expose the balloon 8, which is inflated to a larger diameter by introducing inflation fluid through the lumen 5 of the catheter 4 so it flows out of the opening 10 within the balloon.

Referring to FIGS. 3 and 3a, the inflation of the balloon continues so that the site 26 is dilated by the pressure applied by the balloon. During the inflation, the coating 16 on the balloon is compressed against the site which expels the localizing agent 14 from the coating and into the diseased area. The delivery of the agent 14 under the substantial pressure, for example, 6–8 atmospheres, and simultaneously with the dilatation, injects the agent 14 deep into the plaque and tissue mass at the diseased site. During the dilatation, heat may be applied to the site, which can aid both the dilatation and the delivery of the agent 14 by sealing and smoothing cracks and fissures that are caused by the pressure applied by the balloon. Some of the agent may be sealed into the cracks as the plaque remolds in response to the heat. The agent is present at various depths. Some of the agent 14' is present right at the surface of the plaque, some of the agent 14" is below the surface in the plaque, and some agent 14"' is even delivered into healthy tissue 29 behind the plaque.

Figures 4, 4A:
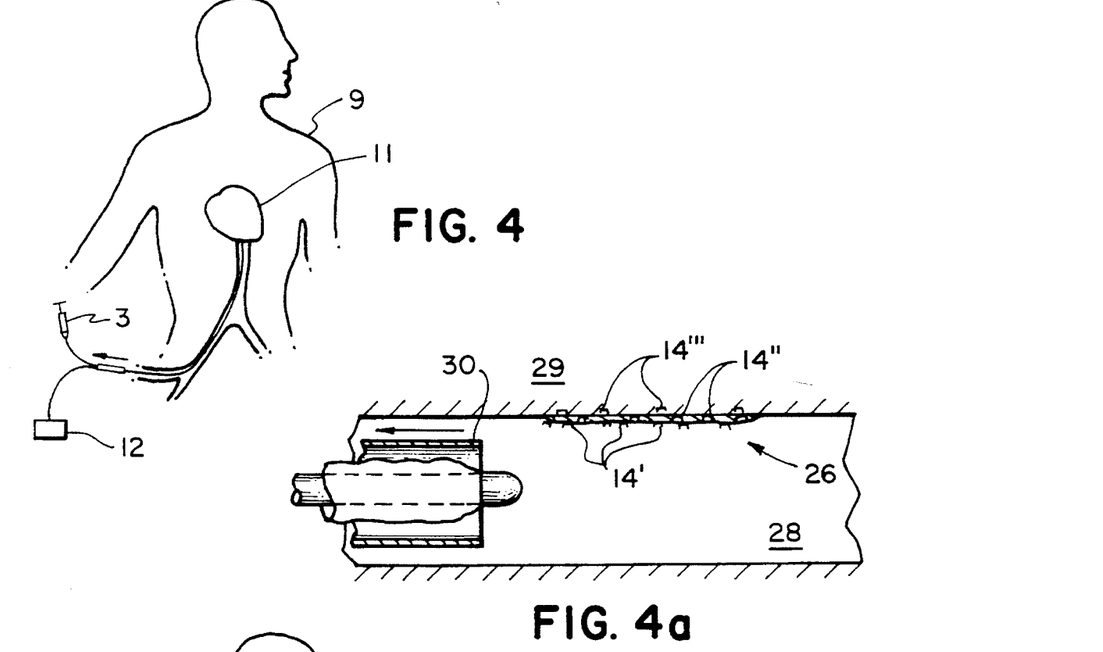

Referring as well to FIGS. 4 and 4a, after the dilatation, the balloon 8 is deflated and the sheath 30 extended over it. The catheter 4 is then removed from the body. The site 26 has been substantially dilated by the treatment and the agent 14 is retained at the site.

Figure 5:
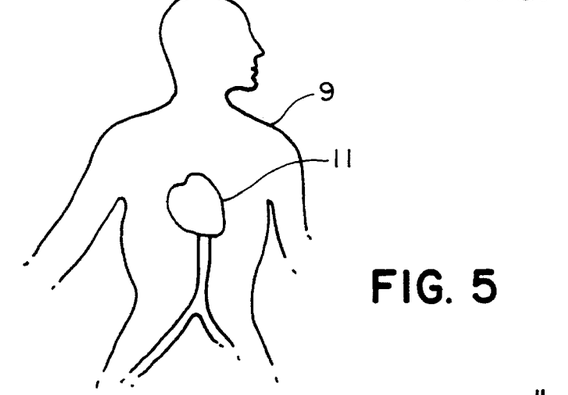
Figure 5A:
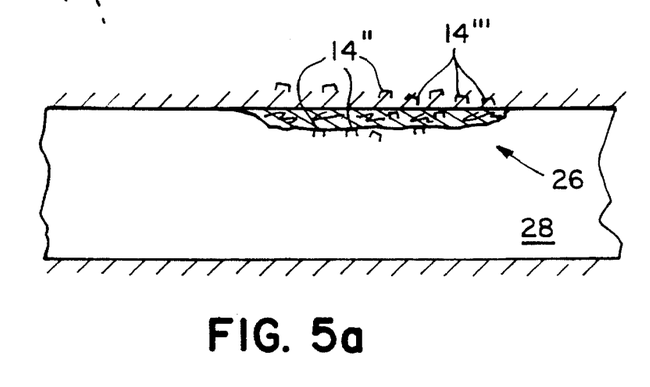

Referring as well to FIGS. 5 and 5a, after the operation, the site 26 may become restenosed. The patient is monitored after the angioplasty operation and restenosis or the onset of restenosis may be detected by visual radiographic observation or by testing samples of physiological fluid or matter for the presence of occluding material or biochemical precursors to restenosis. The restenosis may be caused by the build-up of blood clots which sometimes form on the irregular surfaces that may be created by cracking and so forth during the original dilatation procedure. Clot formation, if it occurs, is typically diagnosed within about 24 hours after the angioplasty operation. The restenosis may also be caused by intimal proliferation, in which the trauma of the dilatation procedure triggers excessive cell growth. Intimal proliferation, if it occurs, is typically diagnosed within 3 to 6 months after the angioplasty operation. In either case, the agent 14 which was delivered during the dilatation, persists at the site.

Figures 6, 6A:
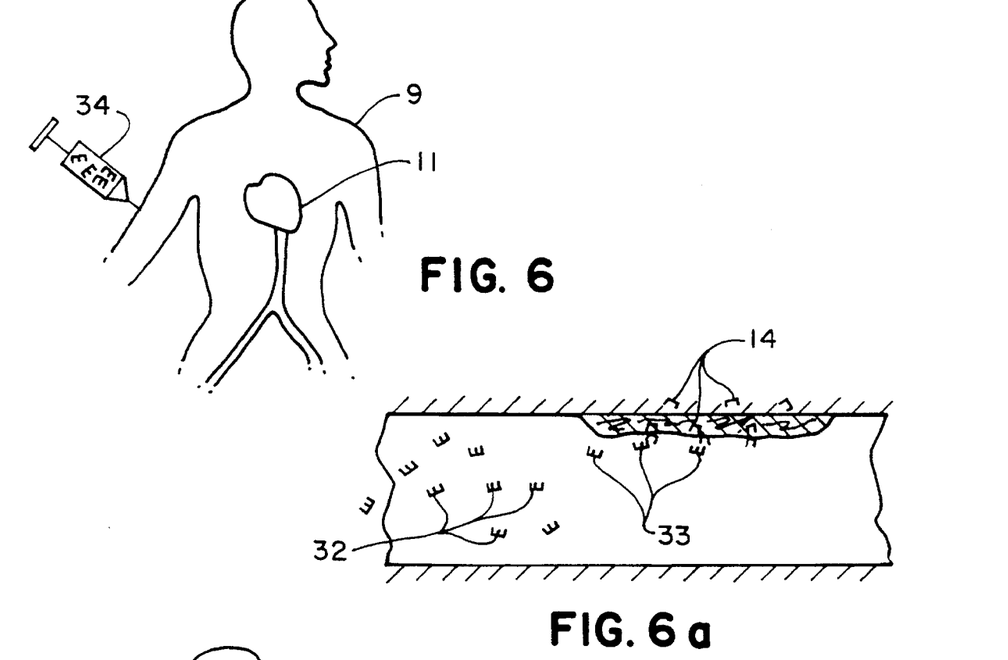

Referring as well to FIGS. 6 and 6a, the restenosis can be treated by systemically delivering a drug that is effective to arrest, prevent, and/or reverse the restenosis and is localized at the site by the localizing agent. The systemic administration of the drug (denoted schematically by ⊔) may be done by intravenous injection using a hypodermic needle 34. The drug 32 travels through the bloodstream to the treatment site where it is localized at the diseased tissue by forming a complex 33 with the agent 14. In this case, the drug administered systemically is heparin, which is provided as an aqueous solution of sodium heparin. Heparin can be localized at the site 26 because it forms a complex with the benzalkonium cation localizing agent. Heparin has both antithrombogenic and antiproliferative properties and therefore may be administered if the restenosis is caused by clot formation, intimal proliferation, or a combination of these causes.

Figures 7, 7A:
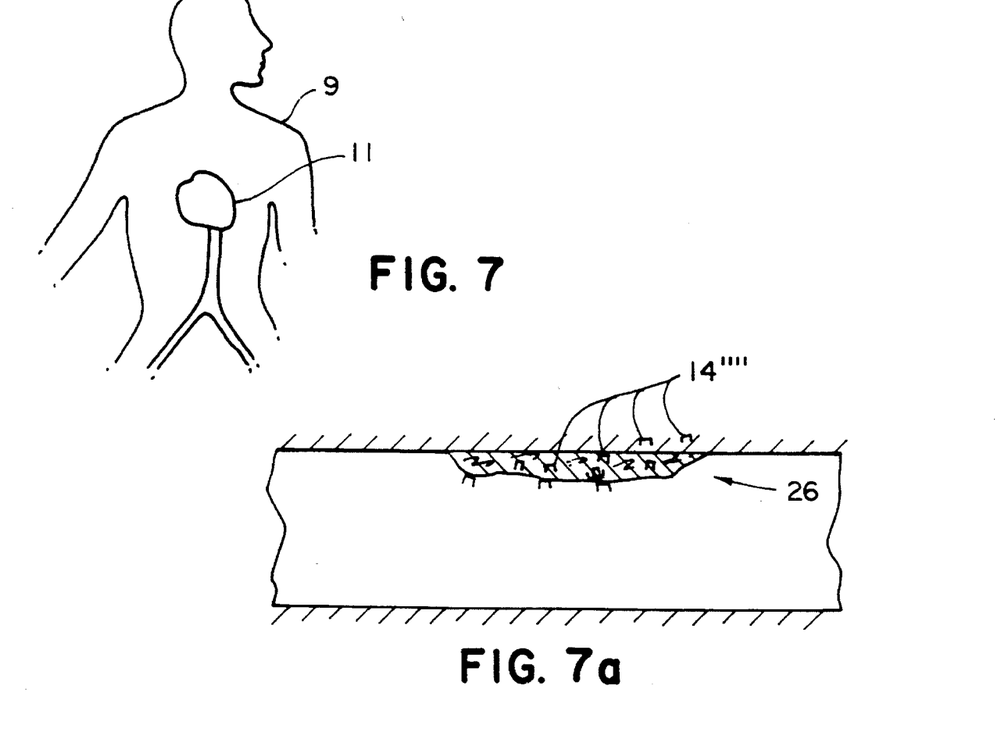

Referring to FIG. 7 and 7a, in time after the systemic administration, the restenosis is treated, e.g. arrested, by the action of the drug 32. The site 26 typically includes surplus agent 14"" which has not been consumed in the initial systemic administration and becomes exposed over time. If restenosis occurs again, more drug can be administered systemically to again treat the site without delivering a medical device into the body of the patient.

A catheter that can be adapted for delivering the localizing agent and carrying out the dilatation is U.S. Pat. No. 5,304,121, the entire contents of which is hereby incorporated by reference. That system is a drug delivery catheter having a swellable, compressible hydrogel coating on a dilatation balloon. The coating may be provided on all of or just a portion of the balloon. Another system is discussed in Wang U.S. Pat. No. 5,254,098, the entire contents of which is also incorporated herein by reference. That system has a balloon that includes channels in the balloon wall through which agent can be flowed and then delivered to the tissue through openings in the channels. The apparatus can be constructed to apply heat to the site by using spaced electrodes within the balloon that are connected to an RF energy control source and inflating the balloon with a conductive saline solution so heat is generated as a result of $I^2R$ losses. A suitable system is discussed in Lennox et al. "Heated Balloon Catheters in the Light" U.S. Pat. No. 4,955,377, the entire contents of which is hereby incorporated by reference. Heat may be applied to mold or adhere the intermediate agent to the treatment site without using dilatation pressure. Ultrasound can also be used to heat the site. Heat may also be used to accelerate the migration or diffusion of the agent from the catheter or within the biological matter at the desired site. The agent may also be delivered by other apparatus. For example, the agent can be delivered on a stent that includes a hydrogel coating. A stent having such a coating is discussed in U.S. Ser. No. 07/795,976, supra. Other agent delivery devices include infusion balloons, a double occlusion balloon where drug agent is delivered between the balloons, and vascular grafts. The patient can be monitored for restenosis or the onset of restenosis by collecting and analyzing samples taken from the dilatation site using techniques taught in U.S. Pat. No. 5,409,012 and Sahatjian, "Bodily Sample Collection" U.S. Ser. No. 08/175, 791, filed Dec. 30, 1993 both of which are incorporated herein by reference. Samples can also be taken from the site using arthrectomy cutters. The site can also be monitored by radiographic techniques, as discussed.

The localizing agent and the drug are selected such that the agent improves the efficacy of the drug at the site, i.e. localizes it, by one or a combination of mechanisms. The agent may act to adhere, i.e., retain the drug at the treatment site. The agent may attract drug in systemic transport to the treatment site. The agent may increase the physiological activity of the drug at the site, e.g., by improving or controlling its transport through matter or into cells. The agent may increase the physiological degradation half-life of the drug at the site. In these ways, the localizing agent may decrease the amount of drug that must be systemically administered compared to systemic administrations without first delivering the agent. The drug must remain in an active state once it is localized by the agent at the site. The agent itself typically does not itself have therapeutic benefit but rather is physiologically inert and innocuous at the levels delivered. (In embodiments, the agent itself may have a therapeutic benefit, which may be different than the benefit from the systemically delivered drug.)

A particular agent/drug combination is benzalkonium cation and heparin to treat clot formation or intimal proliferation, as discussed with respect to the embodiment given above. The capability of benzalkonium cation to localize heparin is believed to arise from electrostatic forces which cause these species to form a complex. Benzalkonium cation is generally cationic and heparin is generally anionic when exposed in an aqueous environment. Other cationic species may be used as the agent for localizing heparin; for example, other ammonium cations. Protamine can be delivered locally as the localizing agent for heparin or heparin-like drugs.

Many other localizing agent and drug combinations may be used. Antibodies may be delivered as localizing agents for protein-based drugs. Messenger RNA or transfer RNA from a genetically engineered DNA can be locally delivered as the agent. Systemically administered DNA couples with the agent RNA and induces cells at the site to produce a beneficial protein. In this case, the DNA-drug is an intermediate species that induces the system to manufacture the desired therapeutic product, the protein. An agent that localizes an antisense genetic strand for restenosis-promoting DNA might also be used. Genetic materials useful in angioplasty procedures are discussed in an application by Sahatjian and Barry, U.S. Ser. No. 08/097,248 filed Jul. 23, 1993, the entire contents of which is hereby incorporated by reference.

The agent may also be act by mechanisms other than electrostatic attraction or by multiple, different mechanisms. For example, the agent may simply adhere to the site and to the drug. A polymer-type drug-localizing agent (e.g. collagen) can be delivered to the site by carrying it on the outside of a balloon and then using pressure and/or heat to release it (e.g. to melt the polymer) from the balloon and to cause it to adhere to the site. The polymer may itself be a localizing agent for a drug or the polymer may act as an adhesive that adheres to the site and includes a drug-coupling specie, e.g. benzalkonium cation, embedded within its matrix and/or attached to its surface that localizes the drug, e.g. heparin, by forming a complex. In the latter embodiment, the agent acts by different mechanisms toward the diseased site and toward the drug: the polymer adheres to the diseased site by melting and coating adherence and the coupling specie has electrostatic complexing properties toward the drug.

Various ailments can be treated. For example, hemodialysis access management can be facilitated by delivering cimetidine to a dialysis shunt site during balloon dilatation of the site and subsequently systemically administering lidocaine to manage pain at the site. Lidocaine forms a complex with cimetidine which exhibits reduced uptake by erythrocytes. (Shibasaki et al., *J. Pharmacobiodyn.*, 11(12) 1988, pp. 785–93.) By using cimetidine as the localizing agent, the efficacy of lidocaine will be improved at the site by reducing the physiological degradation of the drug by erythrocytes. In other examples, tumors may be treated with anticancer drugs. For example, suicide genes, DNA that is activated to kill cells when it couples with specific species, can be localized by locally delivering the coupling species at a tumor site and systemically administering the gene. Moreover, rather than localizing a therapeutic drug, an agent may be delivered locally to localize a systematically administered diagnostic drug, such as a radiopaque or radioactive labelled drug species. Other drugs and treatments are discussed in Sahatjian et al. "Drug Delivery", U.S. Ser. No. 08/097,248, filed Jul. 23, 1993, the entire contents of which is hereby incorporated by reference. Drugs may be delivered that reduce the restenosis, e.g. by killing cells that proliferate to create the occlusion.

The amount of agent locally delivered is dependent on the ability to retain the agent at the site, the toxicity of the agent, the amount of drug needed for an effective dose at the site, the number of sequential systemic administrations that may be needed, and how effectively the agent localizes the drug. For a localizing agent for heparin, such as benzalkonium cation, the amount delivered locally should be sufficient to localize an amount of heparin that has an efficacy equivalent to 10–100 units of non-complexed locally-delivered heparin. Since the drug typically has a particular affinity for the agent, the dose of the drug that is delivered systemically can be reduced, and in some cases, the systemic level of the drug is lowered after it passes the site where the agent has been placed. The amount of heparin administered systemically may be about 5000µ or less per injection.

The localizing agent must be retained at the treatment site. This may be an inherent property of the agent itself which causes it to bind to the biological matter at the site or this may be achieved by the way the agent is delivered. For example, if it is delivered under pressure and/or in combination with heat, it can be mechanically fixed or chemically adsorbed on the surface and moreover, placed deep within the biological matter of the site. The agent placed deeper in the site can migrate to replenish the surface area over time. This assures that agent will be exposed to the flow in the lumen in case prior systemic drug administrations or the flow of body fluid in the lumen removes the agent originally delivered near or at the surface. The localizing agent can also be retained at the site by melting it with a heated balloon, contacting the balloon with the site to transfer the agent to the site, and then removing the balloon, which allows the agent to cool and be retained and adhered at the site. Gelatin or collagen are a meltable polymer materials that can be used in this way. The gelatin may be used as the localizing agent and/or it may incorporate another material, e.g. benzalkonium cation, that acts toward the drug by electrostatic mechanisms. To treat clot formation, the agent should be retained at substantial levels for about 24 hours after angioplasty and to treat intimal proliferation the agent should be retained for 3 to 6 months after angioplasty. The time of agent retention may be less if the drug is administered soon after angioplasty as a preventative measure.

The agent may be delivered simultaneously with dilatation of the vessel as discussed above. Simultaneous with the dilatation and delivery of the agent, a drug, even the drug for which the agent has an affinity, may be delivered, as well. For example, a small dose of heparin may be locally administered simultaneously with delivery of a relatively large amount of ammonium cation during the dilatation. The initial small dose of heparin is effective to inhibit any initial clot formation but is not present at a level sufficient to complex all of the ammonium cation. In time, should restenosis occur either because of later clot formation or intimal proliferation, additional heparin can be administered systemically and localized by the free ammonium cation retained at the site. Similarly, a dose of lidocaine can be administered simultaneously with local delivery of an excess of cimetidine during dilatation of an occluded AV shunt site. The initial dose of lidocaine treats pain during the dilation. Should the patient feel pain after the dilatation, additional lidocaine can be administered systemically.

The agent can also be delivered to the site in a separate step either prior to or after the angioplasty procedure. The agent may be delivered repetitively over time, followed by systemic administrations of the drug. A mixture of different drug-localizing agents can be delivered locally at the same time; then, the different drugs which are localized by the agents can be systemically administered simultaneously or in a desired sequence.

The drug may be administered systemically as needed. As discussed above, the drug may arrest or reverse restenosis after the physician diagnoses it or its onset. If no restenosis is diagnosed, the physician can elect to forego systemic administration of the drug and thus avoid exposing the patient to a physiologically active drug. In time, the relatively physiologically inert or inocuous localizing agent at the site will be metabolized. Alternatively, the drug may be administered prior to diagnosing restenosis as a preventative measure. For example, heparin may be delivered systemically soon after the dilatation so that it is localized at the site and can interfere with the mechanistic pathways that lead to restenosis even before any symptoms that restenosis may occur are observed.

Still further embodiments are within the following claims. For example, the apparatus and methods taught above can be constructed and practiced to treat parts of the body other than the vascular system.

What is claimed is:

1. A method for treating a diseased site in a vascular lumen deep within the body of a patient, comprising:
   (a) providing a drug-localizing agent for a drug that is effective to treat said diseased site,
   (b) providing a medical device capable of being placed into said vascular lumen at said diseased site and capable of delivering said localizing agent locally at said site,
   (c) preparing said medical device for delivering said agent at said site,
   (d) placing said medical device at said site,
   (e) locally delivering said agent to said site in a manner that said agent is retained at said site,
   (f) removing said medical device from said vascular lumen,
   (g) providing said drug effective to treat said diseased site in a form suitable for systemic administration, and
   (h) systematically administering said drug so that said drug is transported through the body of said patient and localized at said diseased site by the presence of said drug-localizing agent retained at said site.

2. The method of claim 1 wherein said agent includes an adhesive polymer that adheres to said site, said polymer incorporating a specie that forms a complex with said drug.

3. The method of claim 1 comprising:
delivering said agent to said site under pressure.

4. The method of claim 1 comprising:
delivering said agent to said site with the aid of heat.

5. The method of claim 1, comprising:
monitoring said patient for symptoms of restenosis after removing the medical device from the vascular lumen, and
providing and administering said drug after observation of said symptoms.

6. The method of claim 1 comprising:
locally delivering a sufficient amount of said agent to localize an effective amount of said drug from multiple sequential systemic administrations, and
systematically administering a sufficient quantity of said drug to effectively treat said site in a sequential fashion as needed.

7. The method of claim 1 comprising:
after systemically delivering a desired drug, delivering additional drug-localizing agent locally to said diseased site and, thereafter systemically delivering additional desired drug.

8. The method of claim 1 comprising:

delivering a mixture of drug-localizing agents effective to concentrate different drugs and systemically administering said drugs as desired.

9. The method of claim 1 wherein said medical device is a dilatation catheter having an expandable portion.

10. The method of claim 1 comprising:

providing a medical device in the form of a dilation catheter having an expandable portion, expanding said expandable portion to dilate said diseased site, and delivering said agent simultaneously with the dilation of said diseased site.

11. The method of claim 10 comprising:

locally administering the same drug that is to be administered systemically.

12. The method of any one of claims 1, 10, or 11 wherein said expandable portion includes a polymer capable of releasing said agent.

13. The method of claim 12 when said polymer is a compressible hydrogel capable of releasing said agent when compressed.

14. The method of claim 12 wherein said expandable portion includes openings or pores or channels through which said agent may pass to deliver said agent to said site.

15. The method of claim 1 said drug forms a chemical complex with said drug-localizing agent.

16. The method of claim 15 wherein said drug is an anionic species and said agent is a cationic species in the body lumen environment of said site.

17. The method of claim 15 wherein said agent is cimetidine and said drug is lidocaine.

18. The method of claim 15 wherein said drug is heparin.

19. The method of claim 18 wherein said agent is an ammonium cation.

20. The method of claim 19 wherein said agent is benzalkonium cation.

21. A method for treating a diseased site in a vascular lumen deep within the body of a patient, comprising:

(a) providing a drug-localizing agent for a drug that is effective to treat said diseased site, (b) providing a medical device capable of being placed into said vascular lumen at said diseased site and capable of delivering said localizing agent locally at said site, (c) preparing said medical device for delivering said agent at said site, (d) placing said medical device at said site, (e) locally delivering said agent to said site in a manner that said agent is retained at said site, (f) removing said medical device from said vascular lumen, (g) monitoring said patient for symptoms of restenosis after removing the medical device from the vascular lumen, and (h) systemically administering said drug to said patient having symptoms of restenosis.

22. A method for treating a diseased site deep within the body, comprising:

locally delivering to said diseased site a drug-localizing agent using a medical device capable of carrying said agent to and releasing said agent at said site in a manner that the agent is retained at the site, removing the medical device from the body, and systemically delivering drug, said drug being localized at said site by the presence of said localizing agent.

23. A kit for delivering a drug-localizing agent to a diseased site in a vascular lumen deep within the body of a patient, comprising:

a drug-localizing agent, in a form suitable for local administration that is retained at said site and is effective for localizing a systemically-administered drug to said site, said agent lacking said drug in a form suitable for local administration, and a medical catheter device sized and constructed for placement into said vascular lumen at said diseased site and for delivering said localizing agent locally at said site in a manner that said agent is retained at said site.

24. A kit for treating a diseased site in a vascular lumen deep within the body of a patient, comprising:

a drug-localizing agent in a form suitable for local administration that is retained at said site and is effective for localizing a systemically-administered drug, said agent lacking said drug in a form suitable for local administration, a drug, in a form suitable for systemic administration, that is effective to treat said diseased site and is localized at said site by prior administration of said localizing agent, and a medical catheter device sized and constructed for placement into said vascular lumen at said diseased site and for delivering said localizing agent locally at said site in a manner that said agent is retained at said site.

25. The method of claim 23 or 24 wherein said medical device is a dilation catheter having an expandable portion.

26. The method of claim 25 wherein said expandable portion includes a polymer membrane capable of releasing said agent.

27. The method of claim 26 when said polymer is a compressible hydrogel capable of releasing said agent when compressed.

* * * * *